(12) United States Patent
Fahmy et al.

(10) Patent No.: US 10,898,593 B2
(45) Date of Patent: Jan. 26, 2021

(54) COMPOSITIONS FOR NANOCONFINEMENT INDUCED CONTRAST ENHANCEMENT AND METHODS OF MAKING AND USING THEREOF

(71) Applicant: Yale University, New Haven, CT (US)

(72) Inventors: Tarek Fahmy, New Haven, CT (US); Albert Sinusas, Guilford, CT (US); Dongin Kim, Glastonbury, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/310,395

(22) PCT Filed: May 13, 2015

(86) PCT No.: PCT/US2015/030468
§ 371 (c)(1),
(2) Date: Nov. 10, 2016

(87) PCT Pub. No.: WO2015/175597
PCT Pub. Date: Nov. 19, 2015

(65) Prior Publication Data
US 2017/0266325 A1    Sep. 21, 2017

Related U.S. Application Data

(60) Provisional application No. 61/992,552, filed on May 13, 2014.

(51) Int. Cl.
| | | |
|---|---|---|
| *A61K 49/04* | (2006.01) | |
| *C08K 9/10* | (2006.01) | |
| *C08J 3/12* | (2006.01) | |
| *A61K 49/18* | (2006.01) | |
| *C08K 3/16* | (2006.01) | |

(52) U.S. Cl.
CPC ...... *A61K 49/0485* (2013.01); *A61K 49/0423* (2013.01); *A61K 49/0438* (2013.01); *A61K 49/0442* (2013.01); *A61K 49/1887* (2013.01); *C08J 3/124* (2013.01); *C08K 3/16* (2013.01); *C08K 9/10* (2013.01)

(58) Field of Classification Search
CPC ............ A61K 49/0485; A61K 49/0423; A61K 49/0438; A61K 49/0442; C08K 3/16; C08K 9/10
See application file for complete search history.

(56) References Cited

U.S. PATENT DOCUMENTS

| | | | | |
|---|---|---|---|---|
| 2006/0002852 A1* | 1/2006 | Saltzman | ............ | A61K 9/0019 424/1.11 |
| 2011/0034422 A1* | 2/2011 | Kannan | ................ | A61K 9/0048 514/152 |
| 2013/0150529 A1* | 6/2013 | Kim | .................... | A61K 49/0442 525/54.1 |

OTHER PUBLICATIONS

Salmso et al., J. Drug Delivery, vol. 2013, Article ID 374252, 1-19 (Year: 2013).*
Cheng, et al., "Developing a highly stable PLGA-mPEG nanoparticle loaded with cisplatin for chemotherapy of ovarian cancer", PLoS One, 6(9):e25433 (2011).
Li, et al., "Iodinated α-tocopherol nano-emulsions as non-toxic contrast agents for preclinical X-ray imaging", Biomaterials, 34:481-91 (2013).
International Search Report for corresponding PCT application PCT/US2015/030468 dated Jul. 28, 2015.
Wang, et al., "Cisplation-alginate conjudgate liposomes for targeted delivery to EGER-positive ovarian cancer c", Biomaterials, 35(14):4297-4309 (2014).
Cheng, et al., "Porous polymersomes with encapsulated Gd-Labeled dendrimers as highly efficient MRI contrast agents", Adv Functional Materials, 19(23):3753-9 (2009).

* cited by examiner

*Primary Examiner* — Robert S Cabral
(74) *Attorney, Agent, or Firm* — Pabst Patent Group LLP (57) ABSTRACT

Multivalent CT or MR contrast agents and methods of making and using thereof are described herein. The agents contain a moiety, such as a polymer, that provides multivalent attachment of CT or MR contrast agents. Examples include, but are not limited to, multivalent linear polymers, branched polymers, or hyperbranched polymers, such as dendrimers, and combinations thereof. The dendrimer is functionalized with one or more high Z-elements, such as iodine. The high Z-elements can be covalently or non-covalently bound to the dendrimer. The dendrimers are confined in order to enhance CT contrast. In some embodiments, the moiety is confined by encapsulating the dendrimers in a material to form particles, such as nanoparticles. In other embodiments, the dendrimer is confined by conjugating the moiety to a material, such as a polymer, which forms a gel upon contact with bodily fluids.

18 Claims, 9 Drawing Sheets

COMPOSITIONS FOR NANOCONFINEMENT INDUCED CONTRAST ENHANCEMENT AND METHODS OF MAKING AND USING THEREOF

CROSS-REFERENCE TO RELATED APPLICATION

This application is a 371 application of International Application No. PCT/US2015/030468, filed May 13, 2015, which claims benefit of U.S. Provisional Application No. 61/992,552, filed May 13, 2014, the disclosure of which is expressly incorporated herein by reference.

STATEMENT REGARDING FEDERALLY SPONSORED RESEARCH

This invention was made with government support under Grant No. U19 203-0025 awarded by the National Institutes of Health. The government has certain rights in the invention.

FIELD OF THE INVENTION

This invention is in the field of compositions for nanoconfinement induced contrast enhancement.

BACKGROUND OF THE INVENTION

Although X-ray-based computed tomography (CT) is one of the most commonly used diagnostic tools in clinical practice, CT is intrinsically poor in discriminating soft tissues with similar effective electron densities, e.g. an early-stage tumor from surrounding tissue, or normal tissue from tissue following ischemic injury. In addition, the relatively high dose of ionizing radiation imparted by the X-rays during CT is carcinogenic, which carries a long-term risk of developing secondary cancers, especially for patients in need of multiple CT scans or with existing health conditions that are sensitive to ionizing radiation.

For these reasons, contrast agents using high atomic number elements, such as iodine, have been used in clinical applications to increase the radiographic contrast of clinical targets in CT. However, despite the increased radiographic contrast obtained with conventional iodinated CT contrast agents, rapid clearance and vascular permeation of these agents leads to short imaging lifetimes, necessitating higher concentrations (~300 mg I/mL) in clinical applications. This level of contrast agent often results in severe adverse side effects in patients, particularly those with impaired renal function, such as nephrotoxicity.

There exists a need for effective contrast agents which exhibit prolonged circulation, minimal vascular permeation, and enhanced CT contrast at lower concentrations than commercially available contrast agents.

Therefore, it is an object of the invention to provide effective contrast agents which exhibit prolonged circulation, minimal vascular permeation, and enhanced CT contrast at lower concentrations than commercially available contrast agents, and methods of making and using thereof.

SUMMARY OF THE INVENTION

Multivalent CT or MR contrast agents and methods of making and using thereof are described herein. The agents contain a moiety, such as a polymer, that provides multivalent attachment of CT or MR contrast agents. Examples include, but are not limited to, multivalent linear polymers, branched polymers, or hyperbranched polymers, such as dendrimers, and combinations thereof. The moiety is functionalized with one or more high Z-elements, such as iodine. The high Z-elements can be covalently or non-covalently bound to the moiety. In some embodiments, the high Z-element is covalently bound. In those embodiments where the high Z-element is covalently bound, the high Z-element can be bound directly to a reactive functional group on the moiety or indirectly (i.e., the high Z-element or elements are bound through a linker or spacer).

The moieties are confined in order to enhance CT or MR contrast. In some embodiments, the moieties are confined by encapsulating the moieties in a material to form particles, such as nanoparticles. In some embodiments, the particle-forming material is a polymer. The polymer is preferably biocompatible and can be biodegradable or non-biodegradable. In some embodiments, the polymer is biodegradable. In particular embodiments, the polymer is an amphiphilic polymer such as block copolymer containing one or more hydrophilic or more hydrophilic blocks, such as a polyalkylene oxide (e.g., PEG) and one or more blocks of a hydrophobic or more hydrophobic polymer, such as an aliphatic polyester (e.g., PLA, PGA, PLGA, etc.).

In other embodiments, the moiety is confined by conjugating the moiety to a material, such as a polymer, which forms a gel upon contact with bodily fluids. In one embodiment, the material is alginate, which is water-soluble absent $Ca^{2+}$ ions but gels in the presence of $Ca^{2+}$ ions. Such conjugates can be used to image disease states having high concentrations of $Ca^{2+}$ ions, such as myocardial infarction.

The particles/conjugates can be combined with one or more pharmaceutically carriers to form pharmaceutical compositions. In some embodiments, the particles/conjugates are administered parenterally as a solution, suspension, or emulsion.

The confinement of the moiety-based contrast agent significantly enhances CT contrast. This allows for the use of lower concentrations of contrast agent, such as iodine, which avoids the toxicity associate with high concentrations of such agents.

DETAILED DESCRIPTION OF THE INVENTION

I. Definitions

"Small molecule," as used herein, refers to molecules with a molecular weight of less than about 2000 g/mol, 1500 g/mol, 1200 g/mol, 1000 g/mol, 750 g/mol, 500 g/mol, or 250 g/mol. In some embodiments, the molecular is weight is from about 250 g/mol to about 500 g/mol.

"Nanoparticle", as used herein, generally refers to a particle having a diameter from about 10 nm up to, but not including, about 1 micron, preferably from about 25 nm to about 1 micron. The particles can have any shape. Nanoparticles having a spherical shape are generally referred to as "nanospheres".

"Molecular weight" as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 15% of the median particle size, more preferably within 10% of the median particle size, most preferably within 5% of the median particle size.

"Nanoconfinement induced contrast enhancement" as used herein means nanoscale proximity of a contrast agent that enables enhancement in the overall contrast. In some embodiments, "nanoconfiment" refers to crowding distances in the range from about 1 to about 20 nanometers. "High Z-element" as used herein refers to elements having a high atomic number typically used as contrast agents.

II. Multivalent Moiety-Based Contrast Agents

Multivalent CT or MR contrast agents and methods of making and using thereof are described herein. The agents contain a moiety, such as a polymer, that provides multivalent attachment of CT or MR contrast agents. Examples include, but are not limited to, multivalent linear polymers, branched polymer, hyperbranched polymers, such as dendrimers, and combinations thereof. Any multivalent/multifunctional system can be used provide it is capable of clustering the contrast agent within nanoscale distances, such as from 1-100 nm, 1-75 nm, 1-50 nm, or 1-25 nm, with separation distances not exceeding 8, 7, 6, 5, 4, 3, or 2 nm.

Confinement of the moiety enhances CT contrast compared to free contrast agent. Such enhancement allows for the use of lower concentrations of contrast agent, which can avoid side effects associated with high concentrations of contrast agents, such as iodine. In some embodiments, the moiety is confined by encapsulating the moiety in a polymer matrix or shell to form nanoparticles. In other embodiments, the moiety is confined by conjugating the moiety to a material, such as a polymer, which forms a gel up contact with biological fluids.

A. High Z-Elements

The compositions described herein can contain one or more moieties functionalized with a plurality of high Z-elements, wherein the moiety is confined in order to enhance CT or MR contrast. Suitable high Z-elements include, but are not limited to, iodine, barium, gadolinium, technetium, gold, bismuth, dysprosium, indium, platinum, or iron/platinum composites. The high Z-element can be covalently or non-covalently bound to the moiety. In some embodiments, the high Z-element is covalently bound to the moiety. In particular embodiments, the high Z-element covalently bound to the moiety is iodine. The high Z-element can be bound directly to a reactive functional group on the moiety or indirectly (i.e., the high Z-element is covalently bound to a reactive functional group on the moiety via a spacer or linker).

B. Dendrimers and Hyperbranched Polymers

"Dendrimer", as used herein, refers to repetitively branched molecules. Dendrimer are typically symmetrical around the core and often adopt a spherical three-dimensional morphology. Dendritic molecules are characterized by structural perfection. Dendrimers are monodisperse and usually highly symmetric, spherical compounds. Dendritic molecules can be divided into low-molecular weight and high-molecular weight species. The first category includes dendrimers and dendrons, and the latter includes dendronized polymers, hyperbranched polymers, and the polymer brush. Hyperbranched polymers are similar to dendrimers except there are one or more imperfections in one or more of the generations, i.e., structural imperfection.

The properties of dendrimers and hyperbranched polymers are typically dominated by the functional groups on the molecular surface; however, there are examples of dendrimers and hyperbranched polymers with internal functionality. Dendritic encapsulation of functional molecules allows for the isolation of the active site, a structure that mimics that of active sites in biomaterials. Also, it is possible to make dendrimers and hyperbranched polymers water soluble, unlike most polymers, by functionalizing their outer shell with charged species or other hydrophilic groups. Other controllable properties of dendrimers and hyperbranched polymers include toxicity, crystallinity, tecto-dendrimer formation, and chirality.

Dendrimers and hyperbranched polymers are typically classified by generation, which refers to the number of repeated branching cycles that are performed during its synthesis. For example if a dendrimer or hyperbranched polymers is made by convergent synthesis, and the branching reactions are performed onto the core molecule three times, the resulting dendrimer is considered a third generation dendrimer. Each successive generation results in a dendrimer roughly twice the molecular weight of the previous generation. Higher generation dendrimers and hyperbranched polymers also have more exposed functional groups on the surface, which can later be used to customize the dendrimer or hyperbranched polymer for a given application.

Suitable dendrimers include, but are not limited to, poly(amidoamine) (PAMAM), arborol, polypropylene imine (PPI) dendrimers, and aromatic dendrimers, such as phenylacetylene dendrimers.

In some embodiments, the dendrimers or hyperbranched polymers contains a plurality of functional groups that can be used to covalently or non-covalently immobilize a high Z-element such as those listed above. In some embodiments, the reactive functional groups on the dendrimer or hyperbranched polymers are amine groups. In some embodiments, the dendrimer is PAMAM. In some embodiments, the PAMAM dendrimer is a generation 4 dendrimer. However, the number of generations can be more or less as necessary. In some embodiments, the high Z-element is iodine which is covalently bound to the dendrimer. In particular embodiments, iodine is covalently bound to a dendrimer by reacting functional groups on the dendrimer, such as amines, with an iodine-containing moiety, such as triiodobenzoic acid (TIBA). Iodine can also be coupled to linear, branched, or hyperbranched (e.g., dendrimers) polymers functionalized with reactive end groups that can be coupled to iodinated agents via amine-carboxyl chemistry or other conjugation chemistries known in the art.

C. Linear and Branched Polymers

The moiety can also be a linear and/or branched polymer, provided the polymer has multiple reactive functional groups to attach the CT or MR contrast agent. Linear and branched polymers having multiple reactive functional groups are known in the art including, but not limited to, multivalent linear or branched oligonucleotides, synthetic polymers, and polypeptides. Examples include linear or branched functional polymers with reactive end groups that couple to iodinated agents via amine-carboxyl chemistry or other conjugation chemistries.

D. Nanoparticles

1. Polymer Matrix/Shell

In some embodiments, the functionalized moiety is encapsulated in a polymer matrix or shell containing one or more polymers to form particles, such as nanoparticles. In some embodiments, the polymer and/or polymers are biocompatible. In other embodiments, the polymer and/or polymers are biocompatible and biodegradable. The polymeric matrix can be selected to degrade over a time period ranging from one day to one year, more preferably from seven days to 26 weeks, more preferably from seven days to 20 weeks, most preferably from seven days to 16 weeks.

By varying the composition and morphology of the polymeric matrix, one can achieve a variety of controlled release characteristics, permitting the delivery of moderate constant doses of one or more active agents over prolonged periods of time.

In general, synthetic polymers are preferred, although natural polymers may be used. Representative polymers include poly(lactic acid), poly(glycolic acid), poly(lactic acid-co-glycolic acids), polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); poly(glycolide-co-caprolactones); polycarbonates such as tyrosine polycarbonates; polyamides (including synthetic and natural polyamides), polypeptides, and poly(amino acids); polyesteramides; other biocompatible polyesters; poly(dioxanones); poly(alkylene alkylates); hydrophilic polyethers; polyurethanes; polyetheresters; polyacetals; polycyanoacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), polyvinyl alcohols, polyvinylpyrrolidone; poly(alkylene oxides) such as polyethylene glycol (PEG); derivatized celluloses such as alkyl celluloses (e.g., methyl cellulose), hydroxyalkyl celluloses (e.g., hydroxypropyl cellulose), cellulose ethers, cellulose esters, nitrocelluloses, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly (phenyl methacrylate), poly(methyl acrylate), poly(isopropyl acrylate), poly(isobutyl acrylate), and poly(octadecyl acrylate) (jointly referred to herein as "polyacrylic acids"), as well as derivatives, copolymers, and blends thereof.

As used herein, "derivatives" include polymers having substitutions, additions of chemical groups and other modifications to the polymeric backbones described above routinely made by those skilled in the art. Natural polymers, including proteins such as albumin, collagen, gelatin, prolamines, such as zein, and polysaccharides such as alginate and pectin, may also be incorporated into the polymeric matrix.

The polymeric matrix may be formed from polymers having a variety of molecular weights, so as to form particles having properties, including drug release rates, optimal for specific applications. Generally, the polymers which make up the polymeric matrix possess average molecular weights of about 2500 to about 1,000,000 Daltons, 2500-500,000 Daltons, 2500-250,000 Daltons, or 2500-100,000 Daltons.

In some embodiments, the polymeric matrix is formed from a poly(alkylene oxide) polymer or a block copolymer containing one or more poly(alkylene oxide) segments. The poly(alkylene oxide) polymer or poly(alkylene oxide) polymer segments may contain between 8 and 500 repeat units, more preferably between 40 and 300 repeat units, most preferably between 50 and 150 repeat units. Suitable poly (alkylene oxides) include polyethylene glycol (also referred to as polyethylene oxide or PEG), polypropylene 1,2-glycol, polypropylene oxide), polypropylene 1,3-glycol, and copolymers thereof.

In some embodiments, the polymeric matrix is formed from an aliphatic polyester or a block copolymer containing one or more aliphatic polyester segments. Preferably the polyester or polyester segments are poly(lactic acid) (PLA), poly(glycolic acid) PGA, or poly(lactide-co-glycolide) (PLGA).

In other embodiments, the matrix is formed from an amphiphilic polymer containing one or more poly(alkylene oxide segments) as the hydrophilic segments and one or more hydrophobic or more hydrophobic segments, such as an aliphatic polyester as described above. In some embodiments, the polymer is a PLGA-PEG block copolymer.

The degradation rate of the polyester segments, and often the corresponding drug release rate, can be varied from days (in the case of pure PGA) to months (in the case of pure PLA), and may be readily manipulated by varying the ratio of PLA to PGA in the polyester segments. In addition, the poly(alkylene oxides), such as PEG, and aliphatic polyesters, such as PGA, PLA, and PLGA have been established as safe for use in humans; these materials have been used in human clinical applications, including drug delivery system, for more than 30 years.

Generally, the average molecular weight of the poly (alkylene oxide) segments is less than or equal to the average molecular weight of the adjoining polyester segments. In certain embodiments, the average molecular weight of the polyester is at least three times greater than the average molecular weight of the poly(alkylene oxide) segment, more preferably at least five times greater than the average molecular weight of poly(alkylene oxide) segment, most preferably at least ten times greater than the average molecular weight of the poly(alkylene oxide) segment. In some embodiments, the molecular weight of the polyakylene oxide segment is from about 500 to about 5,000 Daltons, preferably from about 1,000 to about 5,000 Daltons, more preferably from about 2,500 to about 5,000 Daltons.

In some cases, the central poly(alkylene oxide) segment possesses an average molecular weight ranging between about 500 Da and about 10,000 Da, more preferably between about 1,000 Da and about 7,000 Da, most preferably between about 2,500 Da and about 5,000 Da. In particular embodiments, average molecular weight of the central poly(alkylene oxide) segment is about 4,000 Da. Typically, each adjoining polyester segment possesses an average molecular weight ranging between about 3,000 Daltons to about 50,000 Daltons.

The most widely used are the aliphatic polyesters, specifically the hydrophobic poly(lactic acid) (PLA), more hydrophilic poly(glycolic acid) PGA and their copolymers, poly(lactide-co-glycolide) (PLGA). The degradation rate of these polymers, and often the corresponding drug release rate, can vary from days (PGA) to months (PLA) and is easily manipulated by varying the ratio of PLA to PGA. Second, the physiologic compatibility of PLGA and its homopolymers PGA and PLA have been established for safe use in humans; these materials have a history of over 30 years in various human clinical applications including drug delivery systems. PLGA nanoparticles can be formulated in a variety of ways that improve drug pharmacokinetics and biodistribution to target tissue by either passive or active targeting. The nanoparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. Specifically the hydrophobic poly(lactic acid) (PLA), more hydrophilic poly (glycolic acid) PGA and their copolymers, poly(lactide-co-glycolide) (PLGA) have various release rates. The degradation rate of these polymers, and often the corresponding release rate, can vary from days (PGA) to months (PLA) and is easily manipulated by varying the ratio of PLA to PGA.

E. Conjugates

In other embodiments, the moiety is confined by conjugating the moiety to a material which gels upon contact with bodily fluids. In some embodiments, the material is water-soluble, but gels up contact with bodily fluids due to the presence of one or more gelling agents, such as metal ions (e.g., $Ca^{2+}$). In some embodiments, the material is a polymer.

Suitable materials that gel upon contact with bodily fluids include, but are not limited to, alginate, cellulosic polymers, such as carboxymethyl cellulose, and hyaluronan. In some embodiments, the material is alginate having a molecular weight from about 120,000 to about 190,000 Daltons. Alginate is a soluble polymer in the absence $Ca^{2+}$ ions and gels upon exposure to a Ca2+ in solution. Contrast enhanced imaging of an alginate based system can be applied to several diseases where higher $Ca^{2+}$ ion exist such as myocardial infarction to possibly to track delivery and retention of a therapeutic polymer using NICE.

F. Other Agents

The particles and/or conjugates described above can further contain one or more active agents or prophylactic agents. The agents can be covalent or non-covalently bound or associated with the particles or conjugate or can be encapsulated or distributed within the particles and/or conjugates.

Active agents to be delivered include therapeutic, nutritional, diagnostic, and prophylactic agents. The active agents can be small molecule active agents or biomacromolecules, such as proteins, polypeptides, or nucleic acids. Suitable small molecule active agents include organic and organometallic compounds. The small molecule active agents can be a hydrophilic, hydrophobic, or amphiphilic compound.

Exemplary therapeutic agents that can be incorporated into the particles include tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors (including but not limited to CpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles/conjugates into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

In certain embodiments, the particles include one or more anti-cancer agents. Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®). In certain embodiments, the particles/conjugates include one or more immunomodulatory agents. Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles/conjugates include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A. In a specific embodiment, the immunological adjuvant is MPL. In another embodiment, the immunological adjuvant is LPS. TLR ligands can also include, but are not limited to, TLR3 ligands (e.g., polyinosinic-polycytidylic acid (poly(I:C)), TLR7 ligands (e.g., imiquimod and resiquimod), and TLR9 ligands.

The particles/conjugates may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA ¬ based vaccines are potentially safer than traditional vaccines. DNA vaccines are relatively more stable and more cost-effective for manufacturing and storage. DNA vaccines consist of two major components, DNA carriers (or delivery vehicles) and DNAs encoding antigens. DNA carriers protect DNA from degradation, and can facilitate DNA entry to specific tissues or cells and expression at an efficient level.

G. Targeting Molecules and Molecules Decreasing RES Uptake

The particles and/or conjugates can be modified to facilitate targeting through the attachment of targeting molecules. In the case of particles, the surface of the particles can be modified. In the case of conjugates one or more free reactive groups on the gel-forming material and/or the moiety can be modified to contain one or more targeting moieties.

Exemplary target molecules include proteins, peptides, nucleic acids, lipids, saccharides, or polysaccharides that bind to one or more targets associated with an organ, tissue, cell, or extracellular matrix, or specific type of tumor or infected cell. The degree of specificity with which the particles are targeted can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct nanoparticles to cells and tissues of interest, as well as methods of conjugating target molecules to nanoparticles, are known in the art. See, for example, Ruoslahti, et al. Nat. Rev. Cancer, 2:83-90 (2002). Targeting molecules can also include neuropilins and endothelial targeting molecules, integrins, selectins, and adhesion molecules. Targeting molecules can be covalently bound to particles using a variety of methods known in the art.

In certain embodiments, the particle matrix/shell includes one or more PEGylated polymers, such as block copolymers wherein one or more of the blocks are PEG. The PEG, or other hydrophilic polyalkylene oxide, avoids uptake of the particles by the reticuloendothelial system ("RES"), thereby prolonging in vivo residence time.

The surface of the particles can be modified to facilitate targeting through the attachment of targeting molecules. These can be proteins, peptides, nucleic acid molecules, saccharides or polysaccharides that bind to a receptor or other molecule on the surface of a targeted cell. The degree of specificity can be modulated through the selection of the targeting molecule. For example, antibodies are very specific. These can be polyclonal, monoclonal, fragments, recombinant, or single chain, many of which are commercially available or readily obtained using standard techniques. T-cell specific molecules and antigens which are bound by antigen presenting cells as well as tumor targeting molecules can be bound to the particle (e.g., surface of the particle) or conjugate. The targeting molecules may be conjugated to the terminus of one or more PEG chains present on the surface of the particle.

III. Pharmaceutical Compositions

The particles/conjugates described herein can be combined with one or more pharmaceutically acceptable carriers to prepare pharmaceutical compositions. The compositions can be administered by various routes of administration. However, in some embodiments, the particles are administered parenterally including, but not limited to, intramuscular, intraperitoneal, intravenous (IV) or subcutaneous injection. The particles can be administered locally or systemically.

In a preferred embodiment the particles/conjugates are administered as a solution or suspension by parenteral injection. The formulation can be in the form of a suspension or emulsion. Suitable excipients include, but are not limited to, pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

IV. Methods of Making Particles

A. Functionalized Dendrimers

Dendrimers can be prepared using techniques known in the art or can be purchased commercially. The methodology described below can be used to functionalize amine terminated dendrimers with a high-Z contrast agent, such as iodine.

The dendrimer primary surface amines can be partially acetylated, for example, with sulfo-N-hydroxysuccinimide (NHS)-acetate. TIBA is activated using N,N'-dicyclohexyl carbodiimide (DCC)/NHS and subsequently conjugated to the dendrimer surface to effectively decorate it with iodine. Other agents such as the chelating agent, diethylenetriamine pentacetic acid can be conjugated through an amine functional group (isothiocyanate). DTPA-SCN or other moieties can be conjugated to the iodinated dendrimer via isothiocyanate linkage. Generally other Z-elements can be immobilized through various covalent chemistries to functional groups on the dendrimer.

B. Particles

To encapsulate the iodinate dendrimer (ID) into nanoparticles, ID and a suitable polymer, such as PLGA-PEG, were dissolved in a suitable solvent, such as DMSO. The DMSO solution was transferred to a dialysis membrane (MWCO: 100,000). The dialysis was performed for 24 hours against DI water. Next, the aqueous particle solution was centrifuged and sonicated to concentrate the particle solution. Then, 10 µL of the ID nanoparticle solution was mixed with 990 µL of DMSO to dissolve the nanoparticles and release the ID. The particle size of the nanoparticle or ID was determined using dynamic light scattering (DLS) with a Zetasizer (Malvern).

C. Conjugates

The conjugation of TIBA with PEG can be done using two procedures. Briefly, carboxylated TIBA was activated using DCC/NHS in anhydrous dimethyl sulfoxide (DMSO) and subsequently conjugated to amine group(s) of PEG to yield the TIBA-PEG conjugates.

V. Methods of Use

The particles described herein can be used as computed tomography (CT) contrast agents. X-ray computed tomography (x-ray CT) is a technology that uses computer-processed x-rays to produce tomographic images of specific areas of the scanned object, allowing the user to see what is inside it without cutting it open. Digital geometry processing is used to generate a three-dimensional image of the inside of an object from a large series of two-dimensional radiographic images taken around a single axis of rotation. Medical imaging is the most common application of x-ray CT. Its cross-sectional images are used for diagnostic and therapeutic purposes in various medical disciplines.

Because x-ray CT is the most common form of CT in medicine and various other contexts, the term computed tomography alone (or CT) is often used to refer to x-ray CT, although other types exist (such as positron emission tomography [PET] and single-photon emission computed tomography [SPECT]).

CT produces a volume of data that can be manipulated in order to demonstrate various bodily structures based on their ability to block the x-ray beam. Although, historically, the images generated were in the axial or transverse plane, perpendicular to the long axis of the body, modern scanners allow this volume of data to be reformatted in various planes or even as volumetric (3D) representations of structures. Although most common in medicine, CT is also used in other fields, such as nondestructive materials testing. Another example is archaeological uses such as imaging the contents of sarcophagi.

In general, during a CT scan, incident X-rays are absorbed or scattered to different extents as they traverse different tissues of the body. This differential X-ray attenuation, attributed predominantly to the differences in tissue densities, gives rise to the contrast mechanism exploited by CT. However, the intrinsically low image contrast of soft tissues in Computed Tomography (CT) necessitates the use of contrast agents, often administered at high doses. This mechanism, further exploited by using high atomic number contrast agents such as the commercially available iodinated contrasts agents, suggests that the degree of CT contrast enhancement obtained with iodinated contrast agents is directly proportional to the concentration of iodine present. Therefore, a high local concentration of iodine within a confined volume, "nanoconfinement", may further enhance CT signal-to-noise ratio by increasing the local iodine density. Nanoconfinement-induced Contrast Enhancement or NICE is dependent on nanoscale proximity of iodinated compounds within the confined space suggesting a methodology whereby contrast enhancement can be facilitated with existing compounds through proper engineering of the agent delivery system.

The data described herein demonstrate that geometrical consideration and packaging of conventional agents maybe a powerful modality for increasing CT contrast. One such methodology involves encapsulation of an iodinated agent in biodegradable nanoparticles. This effect is term nanoconfinement induced contrast enhancement (NICE) because the agent is confined within nanoscale proximal distances. Interestingly, confinement of iodine ori the branches of a dendrimer alone led to only minimal increases in comparison with encapsulation of the iodinated dendrimer in a biodegradable nanoparticle. Two factors that influence this enhancement are: a) the concentration of iodine in the confined space and b) the proximity of the iodinated molecules. In the ID case the concentration of agent was not as high as the local concentration within the nanoparticles. Supporting this, aggregates of ID increase CT number compared to solubilized ID. Thus, this effect is due to an increase of local density of iodine within a confined volume.

The data suggest that adjustments to the traditional theory of CT imaging, in which the construction of CT image from 2D x-ray attenuation maps is based on the behavior of x-ray attenuation through bulk materials, may be needed to fully explain the effect of NICE. In the current theory, the "back-projection" of x-ray attenuation maps yields a 3D image of mean "radiodensity" for each voxel of the imaged object. The mean radiodensity of each voxel is measured by the CT number or Hounsfield Unit (HU) defined as $$HU = 1000 \times \frac{\mu - \mu_w}{\mu_w}$$

where $\mu$ and $\mu_w$ represent the mean x-ray linear attenuation coefficients of the voxel and water, respectively. In theory, the value of $\mu$ is determined by the elemental composition of the voxel and, when the elements in the voxel are uniformly distributed, the mean value of $\mu$ would remain the same so long as the concentration of constituent elements is the same. From this perspective, one would expect the CT numbers to be similar for samples containing the same amount of iodine. However, the results clearly demonstrate that the CT number of samples containing the same amount of iodine can be enhanced (significantly) by pulling iodine into nano-scale clusters. This suggests that, in addition to the concentration, the spatial distribution of iodine can also affect a measured CT number. Nanoconfinement-induced CT contrast enhancement (NICE) may have several mechanisms. For example, the clustering of high-Z elements could reduce the negative effects of scattered radiation on the 2D projection image from an otherwise uniformly distributed sample and therefore increase the contrast of the x-ray attenuation maps that were used in CT reconstruction, and resulting in an enhanced CT number compared to the uniformly distributed sample. The confinement of high-Z elements in nano-scale clusters could also increase x-ray attenuation due to the proximity of high-Z elements, which may induce coherent interaction with the x-rays, and thereby enhance measured CT contrast. The effects from these mechanisms are not included in the traditional interpretation of CT reconstructed images.

The multi-fold increase in CT contrast can have several benefits for a wide range of future clinical applications. First, because of an improved resolution and sensitivity, one might be able to decrease the iodine dose given to patients for contrast enhanced CT imaging, lowering the chance of toxicity caused by the high concentration of contrast agents that is applied currently. Alternatively, one could significantly reduce the CT radiation dose while maintaining the same signal intensity provided by currently available commercial iodinated CT contrast agents, thereby decreasing the risk of CT-induced secondary cancer occurrence. With the incorporation of iodine in nanoparticles, there is a higher chance for commercialization because most of the components in the ID nanoparticle are FDA approved. Second, because the end group of nanoparticles can be easily modified by various targeting ligands, one can use these new agents as a specific molecular-based targeting agent for diagnosis, as well as, targeted therapy. This potential integration of diagnostic imaging and therapy has been termed as a "theranostic".

The particles/conjugates described herein can be used to image a variety of tissues, disease states, or pre-disease states, such as tumors, stroke, cardiovascular disease, myocardial infarction, inflammation and diseases characterized by inflammation, autoimmune disorders (e.g., lupus), diabetes, diseases of the central nervous system, such as multiple sclerosis (MS), neurodegenerative disorders, etc.

EXAMPLES

Example 1. Synthesis of Iodinated Dendrimers (ID)

Figure 1A:
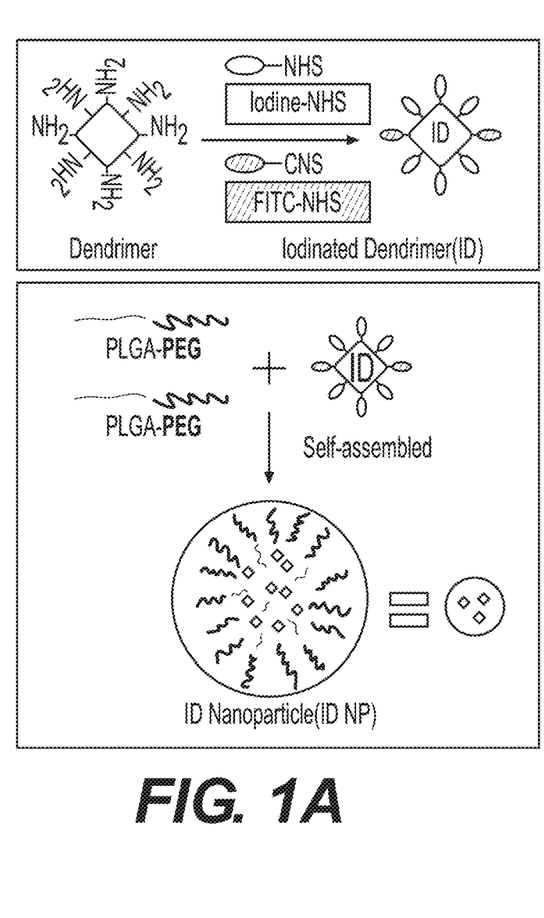
FIG. 1a is a schematic illustration of iodinated dendrimer (ID) synthesis and iodinated dendrimer-nanoparticle (ID-NP) formulation.

Triiodobenzoic acid (TIBA) was conjugated to the amino termini of a generation 4 dendrimer (Diameter32~10 nm, number of branches=64) (FIG. 1a).

The dendrimer primary surface amines were first partially acetylated with sulfo-N-hydroxysuccinimide (NHS)-acetate. Five hundred milligrams of ethylenediamine-core PAMAM generation 4 dendrimers (G4) were desiccated in a 100 mL round-bottom flask and subsequently dissolved in 100 mM sodium bicarbonate buffer (pH 9.0) to a final concentration of 10 mg/mL with magnetic stirring. To this dendrimer solution, 36 mol equiv of sulfosuccinimidyl acetate were added as a solid and allowed to dissolve, The pH of the reaction mixture was immediately adjusted to 8.5 with 1 N NaOH and the reaction was allowed to proceed for 2 h at 25° C. The partially acetylated G4 (G4-Ac) product was purified by ultrafiltration with deionized water using 10K MWCO Amicon Ultra-15 filters and lyophilized to obtain a white crystalline solid.

Two hundred eighty-seven milligrams of 2,3,5-triiodobenzoic acid [TIBA] (18 mol equiv) were added to a 20 mL glass scintillation vial and dissolved in anhydrous dimethyl sulfoxide (DMSO) to a final concentration of 50 mg/mL with magnetic stirring. To the solution of TIBA, 2 mol equiv of both N-hydroxysuccinimide (NHS) and N,N-dicyclohexylcarbodiimide (DCC) were added and allowed to dissolve. The reaction was allowed to proceed for 1 h at 25° C. in the absence of light. The reaction mixture was then filtered with a 0.22 μm PTFE syringe filter to remove the dicyclohexylurea (DCU) reaction byproduct and the filtrate was retained. A three-necked round-bottom flask was charged with 500 mg of G4-Ac and purged with argon. The G4-Ac was then dissolved in 60 mL anhydrous DMSO with magnetic stirring under an argon atmosphere. To this solution, the entire contents of the filtered activated TIBA solution were added via syringe without further purification. The reaction proceeded for 24 h at 25° C. under an argon atmosphere in the absence of light. The reaction mixture was then diluted with 10 volumes of deionized water and subsequently filtered with a 0.22 μm PES vacuum filtration system. The filtrate was purified into deionized water by ultrafiltration using 10K MWCO Amicon Ultra-15 filtrators and lyophilized to obtain a light brown solid.

Six hundred milligrams of G4-Ac-TIBA were added to a 100 mL round-bottom flask and subsequently dissolved in 100 mM sodium bicarbonate buffer (pH 9.0) to a final concentration of 10 mg/mL with magnetic stirring. To this dendrimer solution, 2 mol equiv of 2-(4-isothiocyanatobenzyl)-diethylenetriaminepentaacetic acid (DTPA) and 2 mol equiv of FITC dissolved in anhydrous DMSO were added. The pH of the reaction mixture was immediately adjusted to 8.5 with 1N NaOH, and the reaction proceeded for 18 h at 25° C. in the absence of light. The product was purified by ultrafiltration with deionized water using 10K MWCO Amicon Ultra-15 filtrators and lyophilized to obtain a pale yellow solid.

Example 2. Preparation of Iodinated Dendrimer-Encapsulated Particles

The iodinated dendrimer prepared in Example 1 were encapsulated in a biocompatible, biodegradable polymer to form polymeric nanoparticles (ID-NP). Specifically, the iodinated dendrimers were encapsulated in PLGA-PEG block copolymers using self-assembly (FIG. 1a). The PLGA-PEG block copolymers were prepared using literature procedures.

Acid-terminated PLGA (500 mg) together with 10-fold excess of NHS and DCC were dissolved in 10 mL anhydrous DCM. After being stirred at room temperature for four hours, the reaction solution was filtered through a PTFE filter to remove the precipitate. The NHS-activated PLGA was obtained through precipitation in cold ethyl ether. After dried under vacuum, NHS-activated PLGA was dissolved in anhydrous DCM with equivalent mole of NH2-PEG-COOH and the solution was stirred at room temperature. The conjugate was precipitated in cold ethyl ether and dried under vacuum. To encapsulate ID into nanoparticles, ID and PLGA-PEG polymer were dissolved in DMSO. The DMSO solution was transferred to a dialysis membrane (MWCO: 100,000). The dialysis was performed for 24 hours against DI water.

Example 3. Characterization of Iodinated Dendrimer-Encapsulated Particles

Particle Size

Figure 1B:
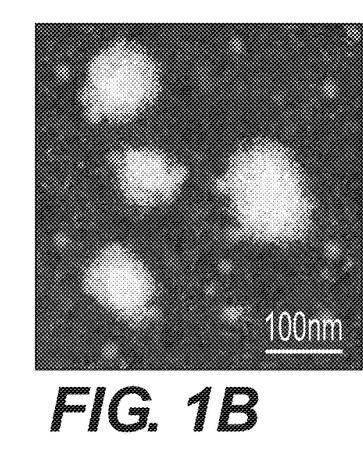
FIG. 1b is a scanning tunneling electron microscopy (STEM) image of ID and ID-NP.
Figure 1C:
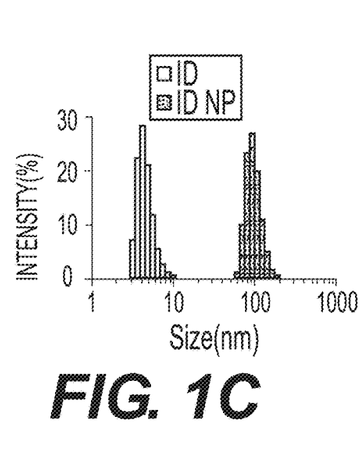
FIG. 1c is a graph showing particle size of ID and ID-NP as measured by DLS.

The diameter of the iodinated dendrimers and the iodinated dendrimer-encapsulated nanoparticles were determined by scanning transmission electron microscopy (STEM) imaging and Dynamic light scattering (DLS). DLS measurements and STEM images showed the particle size of the ID and ID encapsulated nanoparticle (ID NP), ranging from 5-13 nm and 70-135 nm, respectively (FIGS. 1b and 1c).

CT Contrast

Figure 1D:
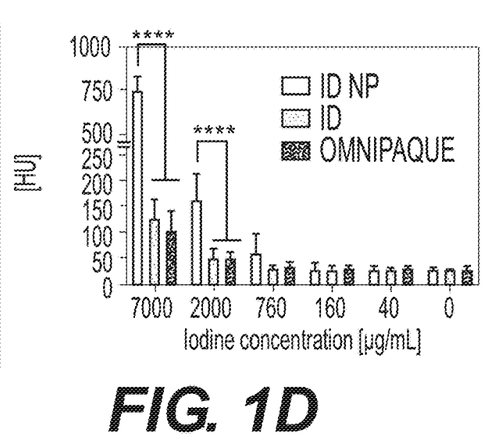
FIG. 1d is a graph showing the CT number of ID-NP, ID, and Omnipaque as determined with micro CT according to different iodine concentrations (n=4, ****P<0.0001 versus ID and Omnipaque and two-way repeated-measures ANOVA with boneferroni test. All data are mean±SD).
Figure 1E:
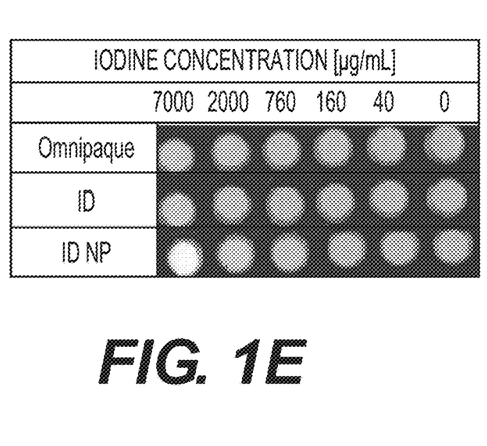
FIG. 1e is X-ray images of each sample from FIG. 1d.

The CT contrast of the ID NP with different iodine concentrations was compared with a commercial CT contrast agent, Omnipaque, using a micro CT (eXplore CT 120, GE Healthcare) (FIGS. 1d and 1e). The CT number of the ID NP at the higher iodine concentration (7 mg/mL) was approximately 750 HU, an increase of more than five-fold over that of ID (~130 HU) or Omnipaque (~100 HU). At a lower iodine concentration of 2 mg/mL, the CT number of the ID NP was approximately 170 HU, whereas the CT numbers of ID or Omnipaque were approximately 50 HU. Thus, the CT number of the ID NP was more than three times higher (FIGS. 1d and 1e).

To validate the generality of this observation, the same samples were scanned on a specimen micro CT (eXplore Locus SP, GE Healthcare) and a clinical 64-slice CT (Discovery NMCT570c, GE Healthcare) with scanning voltages of 50 to 80 kVp and 80 to 140 kVp, respectively (FIG. 2). At 80 kVp, the only setting that is available on both scanners, the CT number measured by the two scanners was consistent for the ID-NP and Omnipaque samples. A more than five-fold increase in CT number was observed for the ID encapsulated nanoparticles (~170 HU) compared to that of the Omnipaque (~30 HU) (FIGS. 2a and 2b) even though the amount of iodine in each sample is approximately the same.

For scanning voltages greater than 80 kVp, the measured CT numbers decreased with increasing kVp (FIG. 2b) for all samples. While, the ratio CT numbers between ID NP and ID or Omnipaque (i.e. contrast enhancement) also decreased with increasing kVp, the rate of reduction was much smaller (FIG. 2d) and the magnitude of contrast enhancement was still greater than five-fold even at 140 kVp. For scanning voltages less than 80, the changes in CT number with decreasing kVp were different among the three samples: with the CT numbers of ID NP and Omnipaque decreased initially till 60 kVp and then increased at 50 kVp while the CT number of ID increased initially and reached a plateau at 60 kVp. The CT contrast enhancement between ID NP and Omnipaque decreased from approximately five-fold at 80 kVp to about two-fold at 50 kVp.

Figure 2A:
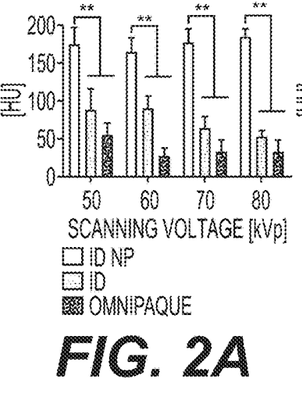
FIGS. 2a and 2b are graphs showing the voltage dependent CT number of ID-NP, ID, and Omnipaque as determined by a specimen CT (FIG. 2a) and clinical CT (FIG. 2b) (n=3, **P<0.01 versus ID and Omnipaque and two-way repeated-measures ANOVA with boneferroni test. All data are mean±SD).
Figure 2B:
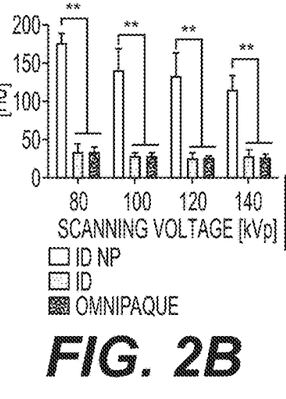
Figure 2C:
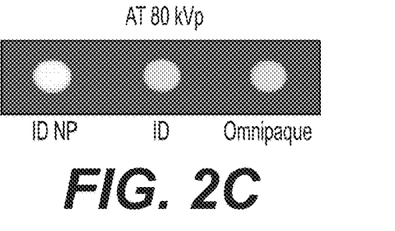
FIG. 2c is clinical CT x-ray images of ID-NP, ID, Omnipaque obtained under 80 Kvp.
Figure 2D:
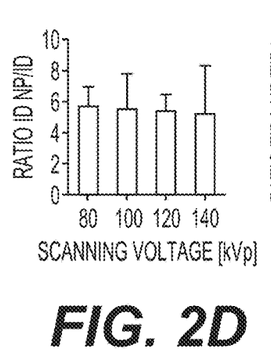
FIGS. 2d and 2e are graphs showing the CT number ratio between ID-NP and NP as determined using CT number from clinical CT according to different voltages. The ratio between TIBA encapsulated NP and TIBA was also determined using the same instrument (n=3, all data are mean±SD).
Figures 2E, 2F:
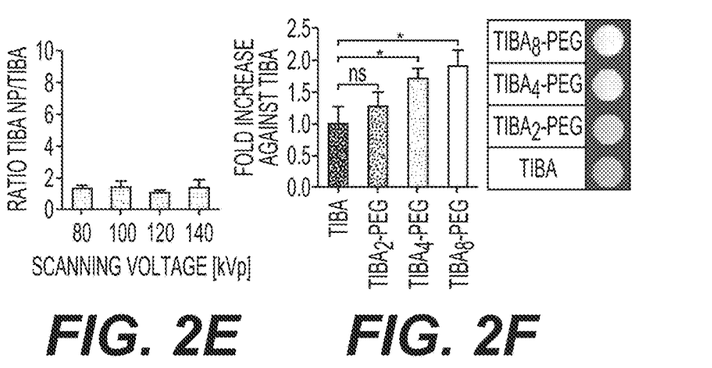
FIG. 2f is a graph showing the influence of the pattern of iodine arrangement within the NP on the CT number and as determined by using the various TIBA conjugated PEG constructs illustrated in FIG. 2g. The concentration of each was set as a 10 mg/mL of TIBA (n=3, *P<0.05 and one-way repeated-measures ANOVA with tukey's multiple comparison test. All data are mean±SD).

To investigate if nanoconfinement-induced contrast enhancement (NICE) can be achieved by facile encapsulation of iodinated molecules in nanoparticles without the intermediate immobilization on dendritic molecules, 2,3,5-triiodobenzoic acid (TIBA) was encapsulated in nanoparticles. The CT number of a sample with TIBA-encapsulated nanoparticles (TIBA NP) was measured and compared with that with TIBA itself. FIG. 2e plots the ratio of CT numbers between TIBA and TIBA NP as a function of kVp. It showed a definite CT number enhancement of less than two-fold, which is less than the five-fold increase observed with ID NP as shown in FIG. 2d. Given that the overall iodine concentration was the same between TIBA NP and ID NP, the observed enhancement suggests that patterns of iodine arrangement within the NP is important, analogue to coherent vs. incoherent interactions of x-rays with a group of iodines.

Figure 2G:
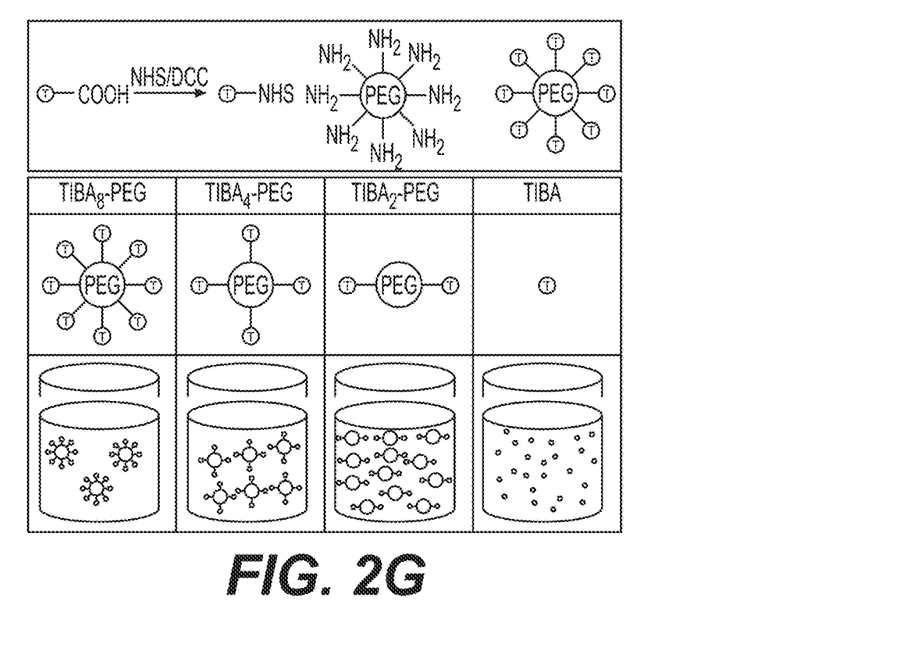
FIG. 2g is a scheme showing the chemical conjugation of TIBA with PEG. TIBA$_2$-PEG represents that TIBA conjugated at the end of linear NH2-PEG-NH$_2$. TIBA$_4$-PEG and TIBA$_8$-PEG also represents that TIBA conjugated at the 4 arms of amine in PEG and 8 arms of amine in PEG, respectively.

To figure out the pattern of iodine arrangement dependent CT number, the CT number of various TIBA conjugated PEGs was determined (FIGS. 2f and 2g). Although TIBA concentration is the same among all samples, it was enhanced according to the increased number of PEG arms and the TIBA conjugated with 8 arm PEG showed the highest CT number. This suggests that the pattern of iodine contributes to NICE.

Figure 3A:
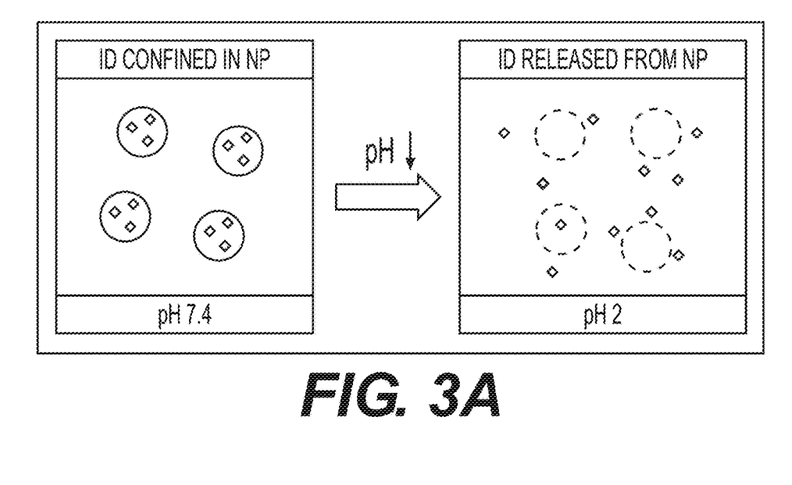
FIG. 3a is a schematic showing the release of iodine as a function of pH.
Figures 3B, 3C:
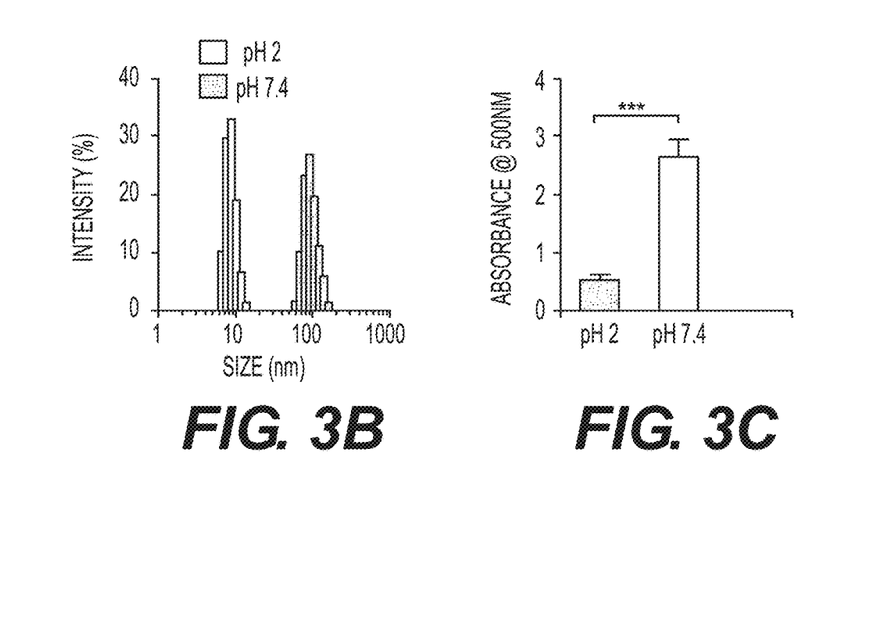
FIGS. 3b and 3c are graphs showing the particle size (FIG. 3b) and the absorbance (FIG. 3c) of ID-NP (5 mg/mL) under pH 2 or 7.4 as determined by DLS.
Figure 3D:
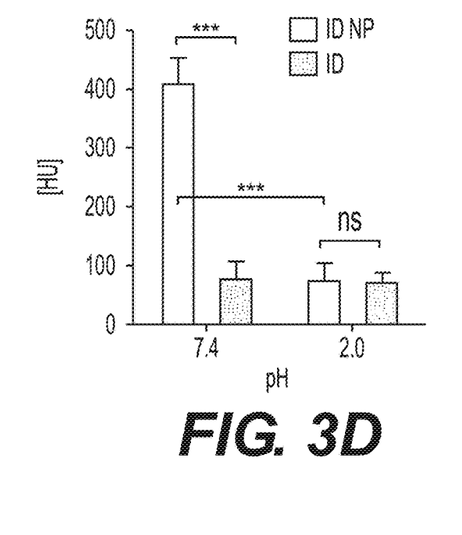
FIG. 3d is a graph showing the CT number of ID and ID-NP (5 mg/mL) under pH 7.4 or pH 2 as obtained by micro CT (n=3, ***P<0.001 versus ID and Omnipaque and two-way repeated-measures ANOVA with boneferroni test. All data are mean±SD).

To further validate NICE, the ID-NP was exposed to pH 7.4 and pH 2 (FIG. 3). At pH 7.4, the ID was stable and remained as intact nanoparticles in suspension. However, at pH 2, it was expected that the nanoparticle would dissolve due to polymer particle accelerated hydrolysis and the iodinated dendrimers would be released. If NICE occurred, the level of x-ray attenuation should be similar to free ID in solution. Using micro CT, the CT number of ID nanoparticle samples at pH 7.4 and pH 2 were measured (FIGS. 3d and 3e). As expected, the CT number of ID nanoparticles in pH 7.4 was enhanced by approximately five-fold compared to ID in pH 7.4, similar to what was observed in FIG. 2. No significant differences in CT contrast were observed between the ID NP and ID at pH 2, indicating that the iodinated dendrimers were released from the biodegradable nanoparticle scaffolding.

To validate this structural change, the particle size was measured in both normal and dissolution (pH 2.0) conditions. Similar to unloaded polymer particles the average particle sizes of ID NP at pH 7.4 was ~100 nm (FIG. 3C. At pH 2 particles were approximately ~7 nm; a size range similar to the released ID. This conclusion was also confirmed using the turbidity at pH 7.4 and pH 2 (FIG. 3c). The turbidity at pH 7.4 was more than five times higher than the turbidity at pH 2, indicating the ID particle at pH 7.4 was stable compared to the disintegrated form at pH 2. These morphological results are consistent with previous results showing thin disk morphology of ID nanoparticles at pH 2; relatively similar to the free dendrimer that was reported previously. However, the granular shape of ID nanoparticles at pH 7.4 indicated stable nanoparticle formation.

Figure 4A:
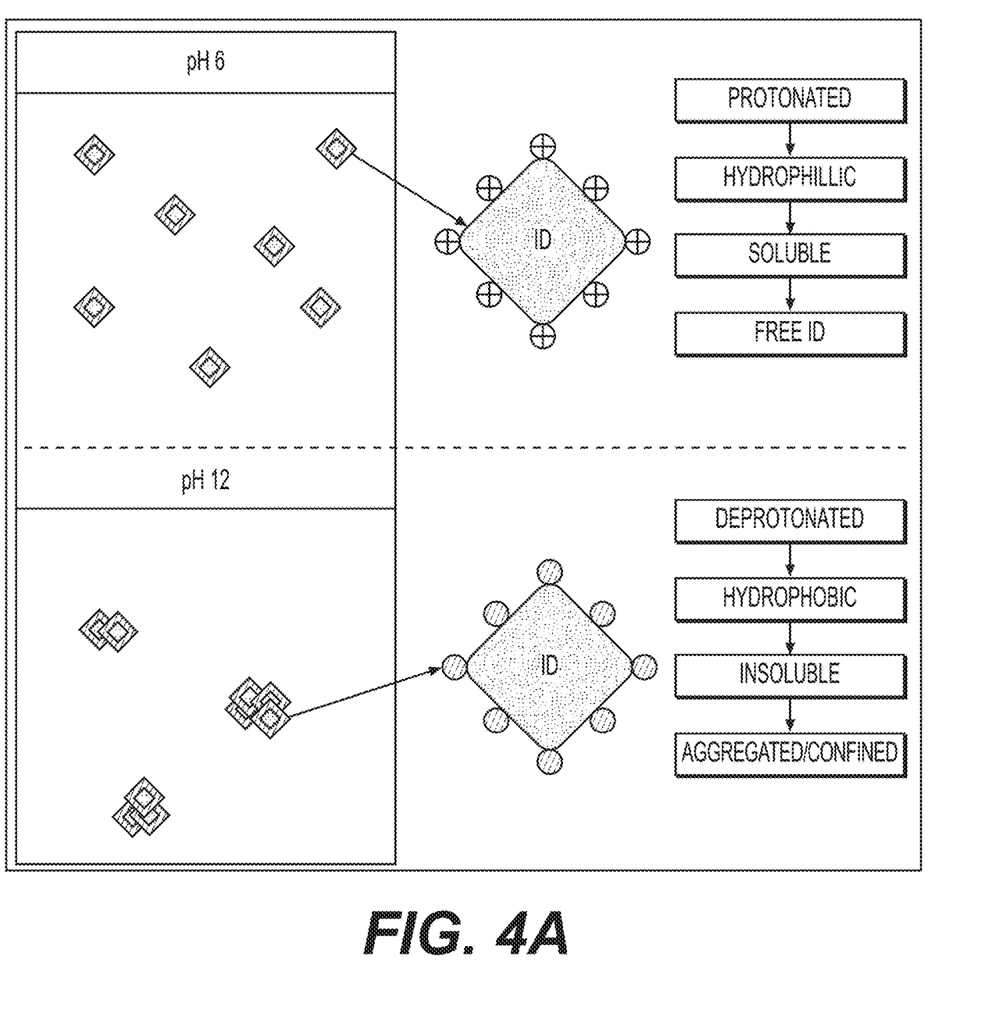
FIG. 4a is a graph showing the ionization state of iodinated dendrimers at pH 6 and 12.
Figure 4B:
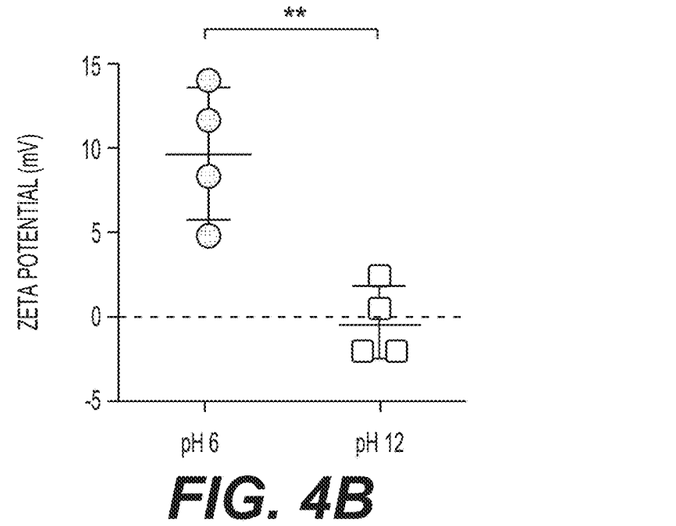
FIG. 4b is a graph showing the zeta potential of iodinated dendrimers at pH 6 and 12.
Figure 4C:
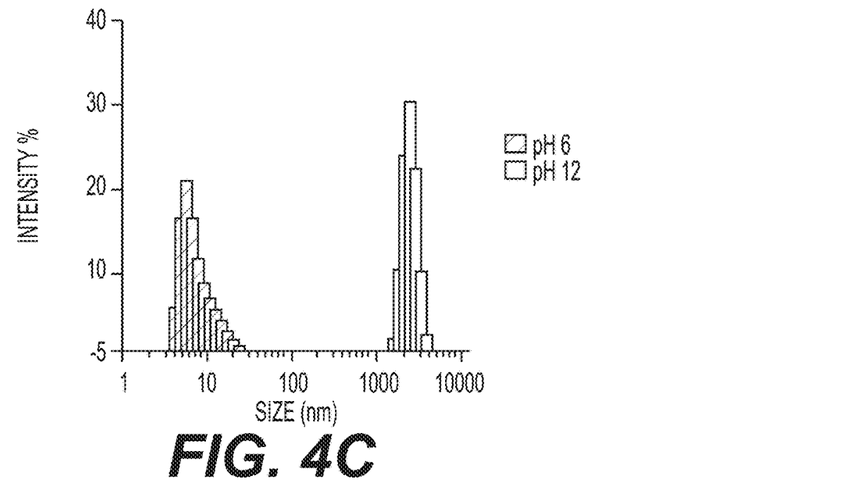
FIG. 4c is a graph showing particle size of iodinated dendrimers as a function of pH (6 and 12).
Figure 4D:
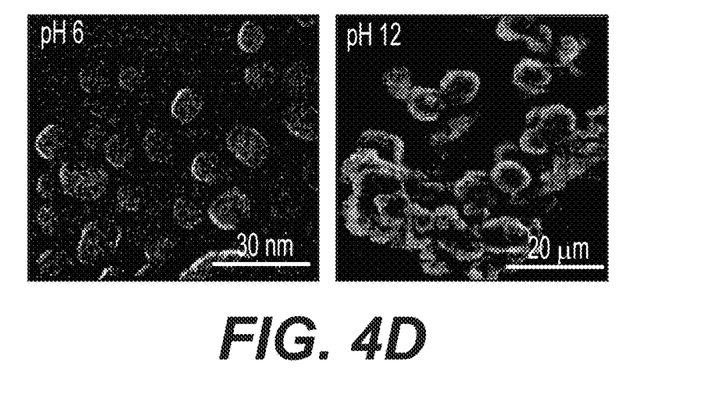
FIG. 4d is an STM image of iodinated dendrimer particles at pH 6 and 12.
Figure 4E:
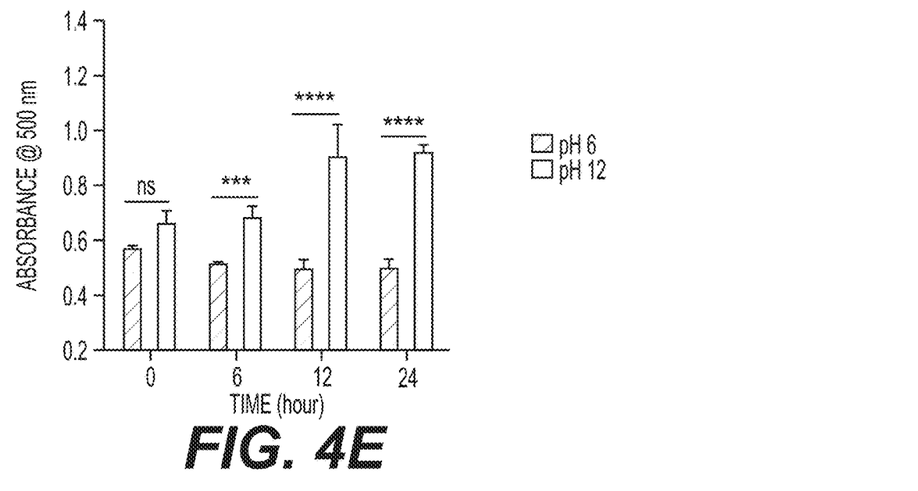
FIG. 4e is a graph showing absorbance at 500 nm of iodinated dendrimers as a function of time (hours) at pH 6 and 12.
Figure 4F:
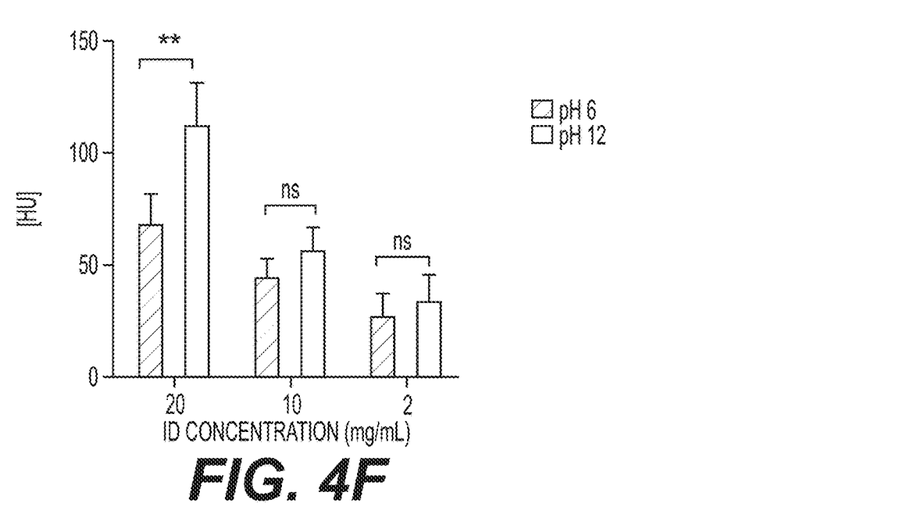
FIG. 4f is a graph showing CT number as a function of pH for iodinated dendrimers.
Figure 4G:
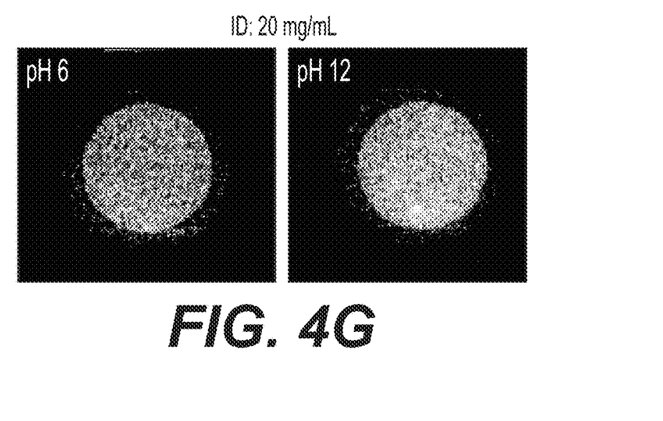
FIG. 4g is an STM image of iodinated dendrimers at a concentration of 20 mg/ml at pH 6 and 12.

The results above indicate that x-ray attenuation is influenced by the degree of contrast agent aggregation. Given that the free amines on an iodinated dendrimer have a pKa 7~9, it was hypothesized that at pH 6 the ID would be protonated and therefore solubilized and conversely deprotonation would occur at pH 12 and form aggregate clusters. To validate the effect of protonation on ID aggregation, surface charge (zeta potential) measurements of the ID in pH 6 and 12 buffered solutions were measured (FIG. 4a). Furthermore, an increase in the turbidity and particle size of the ID in basic solutions and conversely a decrease in turbidity and aggregate size under acidic pH validated this effect (FIGS. 4b, 4c, and 4d). It was found that the CT number of dendrimers in basic pH was also higher compared to CT numbers in acidic pH (FIGS. 4e and 4f), which supports the conclusion that the clustering of ID can lead to an increase in CT contrast enhancement and this may be induced by aggregation of the ID in solution or by confinement in a nanoparticle (FIG. 3).

Example 4. Preparation of Iodinated Dendrimer-Coupled Alginates

Iodinated dendrimers were coupled to alginate which is sensitive to $Ca^{2+}$ in solution for two different sets of polymers (FIG. 5).

The synthesis of alginate-ID was carried out using NHS with 1-ethyl -3-(3-dimethylaminopropyl) carbodiimide hydrochloride (EDC). Briefly, 10 mg of alginate-COOH was pretreated with 1 mL of deionized (DI) water for 1 hour in order to dissolve the material. Then 100 µL of NHS stock solution (1.9 mg/mL of DI water), 100 µL of EDC stock solution (3.3 mg/mL of DI water), and 100 µL of ID stock solution (10 mg/mL of DI water) was added into pre-activated alginate-COOH water solution and keep overnight to complete the reaction for. On the next day, the conjugate was purified using ultracentrifugation (MWCO 10000), which was followed by freeze-drying. Alginate-ID was treated with different concentration of $CaCl_2$ DI $H_2O$ solution. FITC or Rhodamine or both FITC and Rhodamine decorated ID was conjugated with alginate using similar method as above for fluorescence energy transfer (FRET) study.

Figure 5A:
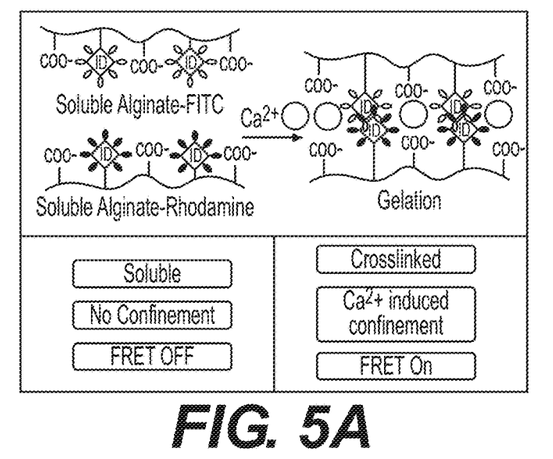
FIG. 5a is a schematic illustration of $Ca^{2+}$ ion sensitive alginate FRET system.
Figure 5B:
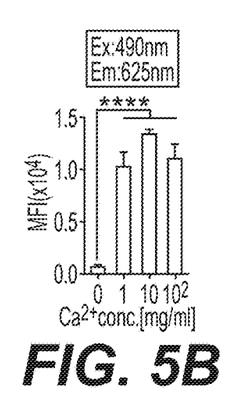
FIG. 5b is a graph showing the emission intensity of rhodamine upon the mixture of alginate-FITC with alginate-Rhodamine as determined during excitation of FITC according to different $Ca^{2+}$ ion concentration (n=3, *P<0.001 and one-way repeated-measures ANOVA with tukey's multiple comparison test. All data are mean±SD).
Figure 5C:
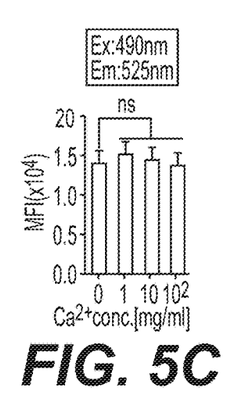
FIG. 5c is a graph showing the emission intensity of FITC was determined during excitation of FITC (n=3, *P<0.001 and one-way repeated-measures ANOVA with tukey's multiple comparison test. All data are mean±SD).
Figure 5D:
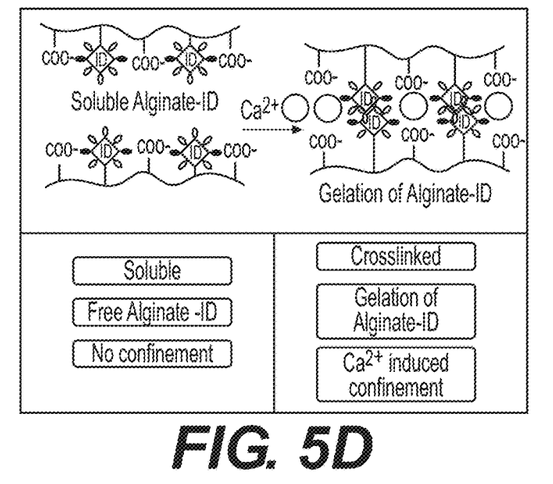
FIG. 5d is a schematic illustration of alginate-ID.
Figure 5E:
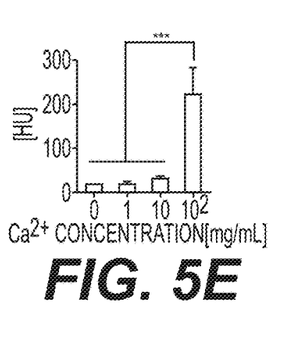
FIG. 5e is a graph showing the CT number of alginate-ID as determined using micro CT under different Ca2+ ion concentrations (n=3, ***P<0.001 and one-way repeated-measures ANOVA with boneferroni test. All data are mean±SD).

Alginate is a soluble polymer in the absence $Ca^{2+}$ ions and gels upon exposure to $Ca^{2+}$ ions in solution. Fluorescence energy transfer (FRET) was used to assess the level of proximity needed for the observed effects. In FRET, the emission intensity of the acceptor upon excitation of the donor is inversely proportional to the distance between donor and acceptor dyes. FRET between IDs labeled with donor (fluorescein) on one set of alginate polymers and acceptor (rhodamine) fluorophores on a different set of polymers confirmed a change in the proximity of the ID upon addition of $Ca^{2+}$ (FIG. 5a). As shown in FIGS. 5b and 5c, the emission intensity of rhodamine under FITC excitation is minimal in the absence of $Ca^{2+}$ ions and is significantly enhanced with the addition of $Ca^{2+}$ ions. This induced proximity enhanced the CT number (FIG. 5d). As shown in FIGS. 5d, 5e, and 5f, the CT number is significantly enhanced in an ion dose dependent manner. The results from these studies highlight the importance of proximity and clustered confinement of iodinated agents for contrast enhancement in CT.

Example 5. Incorporation of Magnetite into PLGA Nanoparticles

Figure 6A:
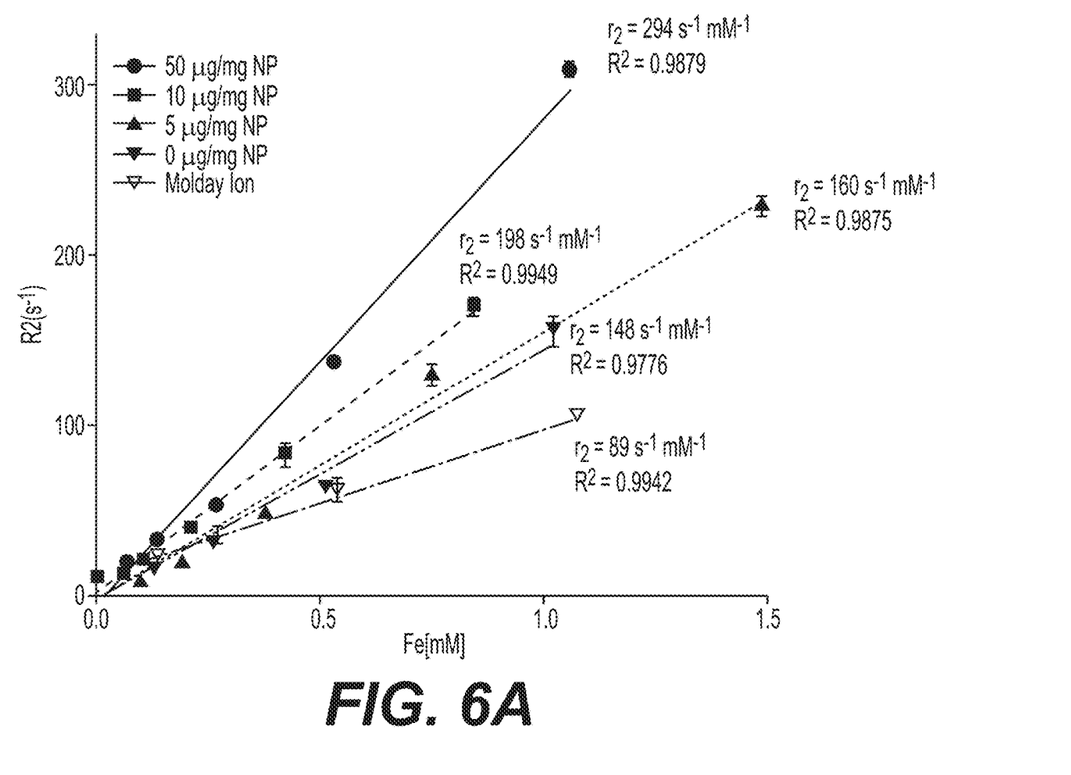
FIG. 6a is a graph showing the R2 as a function of iron (Fe) concentration.

To demonstrate that incorporation of hydrophobic magnetite into PLGA nanoparticles did not deter the system's imaging capabilities, T2-weighted images of samples in PBS with decreasing particle concentrations were measured at room temperature in triplicate. The r2 was determined by the slope of a linear fit of 1/T2 versus iron concentration (FIG. 6a). The r2 value of the avidin-functionalized superparamagnetic iron oxide (SPIO)-PLGA nanoparticles (294 mM-1S-1) was greater than unmodified SPIO-PLGA nanoparticles (160 mM-1S-1) and both were observed to be higher than that of commercially available iron oxide nanoparticles, Molday Ion (BioPal, USA) (89 mM-1S-1).

Figure 6B:
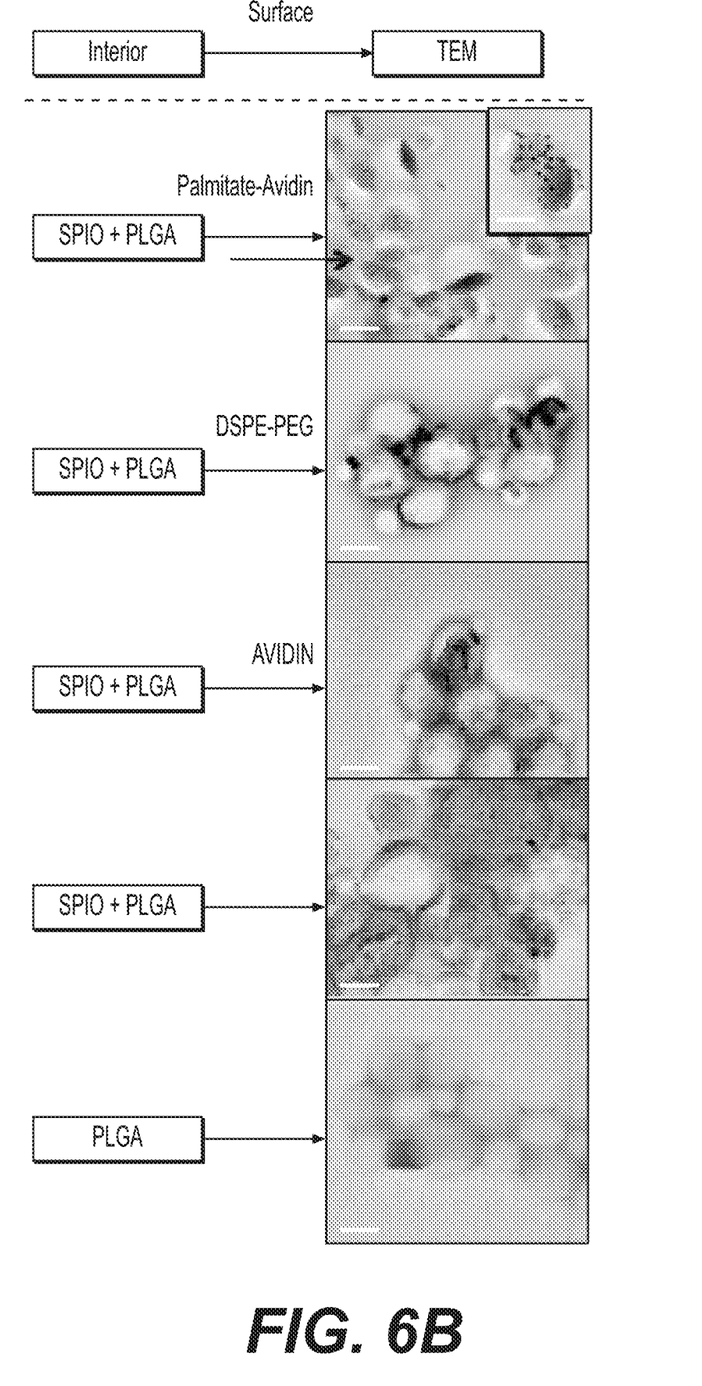
FIG. 6b are TEM images for different functionalized particles.

It was noted that increasing concentrations (0, 5, 10, 50 µg/mL) of palmitate-avidin resulted in increased relaxivities. TEM revealed loading of discrete SPIO into PLGA nanoparticles (FIG. 6b). DSPE-PEG was used to further validate the observation that a hydrophobic tail, besides a fatty acid, can be used to induce clustering of the fatty acid modified iron-oxide in PLGA particles during emulsion formation (FIG. 6b). The size difference (hydrodynamic diameter) between the hydrophobic tail and the hydrophilic component of DSPE-PEG approximately (1 nm DSPE: 4-5 nm PEG) is similar to the size difference of palmitic acid-avidin (~1 nm palmitic acid: 5 nm avidin). Nanoparticles fabricated with and without soluble avidin showed no aggregation proving that the aggregation was not a function of the presence of avidin. TEM of blank PLGA nanoparticles served as a control.

The results demonstrate that fatty acid modified iron oxide prolonged retention of the contrast agent in the polymer matrix during degradative release of drug. Antibody-fatty acid surface modification facilitated cellular targeting and subsequent internalization in cells while inducing clustering of encapsulated fatty-acid modified SPIO during particle formulation. This induced clustered confinement led to an aggregation within the nanoparticle and hence, higher transverse relaxivity, r2, (294 mM-1 s-1) compared to nanoparticles without fatty-acid ligands (160 mM-1 s-1) and higher than commercially available SPIO nanoparticles (89 mM-1S-1).

We claim:

1. A pharmaceutical composition comprising polymeric nanoparticles having an average diameter between about 50 and about 150 nm, wherein the nanoparticles comprise
    one or more encapsulating polymers selected from the group consisting of polycaprolactone, polylactic acid, polyglycolic acid, and copolymers thereof and amphiphilic polymers selected from the group consisting of poly(lactic acid)-polyethylene glycol (PLA-PEG), poly(glycolic acid)-polyethylene glycol (PGA-PEG), and poly(lactide -co-glycolide)-polyethylene glycol (PLGA-PEG); and
    one or more multifunctional polymers selected from the group consisting of hyperbranched polymers, dendrimers, multifunctional linear polymers, and combinations thereof, the multifunctional polymers having attached covalently or non-covalently thereto one or more elements selected from the group consisting of iodine, barium, gadolinium, gold, bismuth, dysprosium, platinum, and combinations thereof;
    wherein the multifunctional polymers are encapsulated within the polymeric nanoparticles such that the elements are clustered at distances of between about 1 and about 100 nm, and
    wherein the concentration of the elements in the polymeric nanoparticles is between about 500 and about 10,000 µg/ml,
    wherein the elements within the polymeric nanoparticles are at an effective amount and clustering distance to enhance computed tomography contrast, as compared to a control composition having the same concentration of the elements not in the same clustering distances.

2. The composition of claim 1, wherein the one or more multifunctional polymers are hyperbranched polymers.

3. The composition of claim 1, wherein the nanoparticles comprise amphiphilic polymers and are formed by self-assembly.

4. The composition of claim 3, wherein the amphiphilic polymers are pegylated copolymers of polymers selected from the group consisting of polycaprolactone, polylactic acid, polyglycolic acid, and copolymers thereof.

5. The composition of claim 4, wherein the pegylated copolymers are selected from the group consisting of poly(lactic acid) -polyethylene glycol (PLA-PEG), poly(glycolic acid)-polyethylene glycol (PGA-PEG), and poly(lactide-co-glycolide)-polyethylene glycol (PLGA-PEG).

6. The composition of claim 3, wherein the amphiphilic polymer comprises pegylated polycaprolactone.

7. The composition of claim 1, wherein the elements comprise iodine.

8. The composition of claim 1, wherein the multifunctional polymers are polyamidoamine (PAMAM) dendrimers.

9. The composition of claim 1, wherein contrast enhancement by the nanoparticles in computing tomography at pH 7.4 is at least two-fold, three-fold, four-fold, five-fold or greater as compared to the control composition.

10. The composition of claim 1, wherein the nanoparticles further comprise one or more therapeutic agents, prophylactic agents, nutraceuticals, or combinations thereof.

11. The composition of claim 1, wherein the nanoparticles further contain a targeting moiety.

12. The composition of claim 1, further comprising one or more pharmaceutically acceptable carriers.

13. A method for imaging soft tissue using computing tomography, comprising
    administering to the soft tissue an effective amount of the composition of claim 1, and imaging the soft tissue using computing tomography.

14. The method of claim 13, wherein the composition is administered parenterally.

15. The nanoparticles of claim 1, wherein the elements within the polymeric nanoparticles are at distances of between about 1 and about 75 nm.

16. The composition of claim 1, wherein the elements within the polymeric nanoparticles are clustered at distances of between about 1 and about 50 nm.

17. The composition of claim 1, wherein the elements within the polymeric nanoparticles are clustered at distances of between about 1 and about 25 nm.

18. The composition of claim 1, wherein the elements within the polymeric nanoparticles are clustered at distances less than about 8, 7, 6, 5, 4, 3, or 2 nm.

* * * * *